United States Patent
Tanaka et al.

(10) Patent No.: US 9,345,904 B2
(45) Date of Patent: May 24, 2016

(54) PHOTODYNAMIC THERAPY USING PHOTOSENSITIZING AGENT OR 5-AMINOLEVULINIC ACID

(75) Inventors: Tohru Tanaka, Tokyo (JP); Katsushi Inoue, Tokyo (JP); Takuya Ishii, Tokyo (JP); Takato Yoshida, Yokohama (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 220 days.

(21) Appl. No.: 14/126,929

(22) PCT Filed: Jun. 20, 2012

(86) PCT No.: PCT/JP2012/003995
§ 371 (c)(1),
(2), (4) Date: Dec. 17, 2013

(87) PCT Pub. No.: WO2013/005379
PCT Pub. Date: Jan. 10, 2013

(65) Prior Publication Data
US 2014/0128799 A1 May 8, 2014

(30) Foreign Application Priority Data
Jul. 1, 2011 (JP) .................................. 2011-147711

(51) Int. Cl.
*A61K 41/00* (2006.01)
*A61N 5/06* (2006.01)
(Continued)

(52) U.S. Cl.
CPC ............. *A61N 5/062* (2013.01); *A61K 31/197* (2013.01); *A61K 41/0061* (2013.01); *A61K 41/0071* (2013.01); *A61K 49/0052* (2013.01)

(58) Field of Classification Search
CPC .......................... A61N 5/062; A61K 41/0061
See application file for complete search history.

(56) References Cited

U.S. PATENT DOCUMENTS

| 6,034,267 A * | 3/2000 | Gierskcky .......... A61K 41/0061 424/9.6 |
| 2002/0004053 A1* | 1/2002 | Biel ....................... A61K 39/39 424/277.1 |

(Continued)

FOREIGN PATENT DOCUMENTS

| JP | 11-012197 A | 1/1999 |
| JP | 2004-532251 A | 10/2004 |

(Continued)

OTHER PUBLICATIONS

Alvanopoulos et al., "Photodynamic therapy of superficial basal cell carcinomas using exogenous 5-aminolevulinic acid and 514-nm light," Journal of the European Academy of Dermatology and Venereology, 1997, 9:134-136.

(Continued)

*Primary Examiner* — Lynsey Crandall
(74) *Attorney, Agent, or Firm* — Foley & Lardner LLP

(57) ABSTRACT

It is to provide photodynamic therapy (PDT) and photodynamic diagnosis (PDD) which are suitable for the diagnosis and therapy of a part requiring a certain degree of deep penetration, such as subcutaneous cancer and lymph nodes surrounded by blood vessels and fat. This is solved by performing PDT and PDD targeting cancer by administering a composition comprising a photosensitizing agent such as a tetrapyrrole-based compound (photofrin, protoporphyrin IX, etc.) or ALAs such as 5-aminolevulinic acid (ALA), ALA methyl ester, ALA ethyl ester, ALA propyl ester, ALA butyl ester, ALA pentyl ester, or a hydrochloride, phosphate, or sulfate thereof followed by irradiation with excitation light at a wavelength of 480 to 580 nm.

3 Claims, 3 Drawing Sheets

(51) Int. Cl.
*A61K 31/197* (2006.01)
*A61K 49/00* (2006.01)

(56) References Cited

U.S. PATENT DOCUMENTS

| | | | | |
|---|---|---|---|---|
| 2002/0087205 | A1* | 7/2002 | Chen | A61K 41/0057 607/88 |
| 2003/0176411 | A1* | 9/2003 | Voet | A61K 31/409 514/185 |
| 2004/0096425 | A1* | 5/2004 | Hogset | A61K 41/0057 424/93.2 |
| 2007/0072933 | A1* | 3/2007 | Peyman | A61K 31/404 514/414 |
| 2009/0176881 | A1 | 7/2009 | Oh et al. | |
| 2009/0259167 | A1* | 10/2009 | Sakamoto | A61K 31/197 604/21 |
| 2009/0287195 | A1* | 11/2009 | Altshuler | A61H 99/00 606/9 |
| 2011/0034854 | A1* | 2/2011 | Neuberger | A61N 5/062 604/20 |

FOREIGN PATENT DOCUMENTS

| | | |
|---|---|---|
| JP | 2005-132766 A | 5/2005 |
| JP | 2005-349028 A | 12/2005 |
| JP | 2005-350418 A | 12/2005 |
| JP | 2006-034375 A | 2/2006 |
| JP | 2006-182753 A | 7/2006 |
| JP | 2007-015938 A | 1/2007 |
| JP | 2007-509034 A | 4/2007 |
| JP | 2008-208072 A | 9/2008 |
| JP | 2009-539971 A | 11/2009 |
| JP | 2009-542801 A | 12/2009 |
| JP | 2010-163445 A | 7/2010 |
| JP | 2011-001307 A | 1/2011 |
| WO | WO 02/096366 A | 12/2002 |
| WO | WO 2005/032459 A2 | 4/2005 |
| WO | WO 2008/004847 A1 | 1/2008 |

OTHER PUBLICATIONS

Chen et al., "Endogenous photodynamic therapy on SW480 human colon cancer xenografts in athymic mice," Chin. J. Exp. Surg., Nov. 2004, 21(11):1331-1332.
Frei et al., "Photodynamic detection of diseased axillary sentinel lymph node after oral application of aminolevulinic acid in patients with breast cancer," British Journal of Cancer, 2004, 90:805-809.
Iinuma, Seiichi, "Basic research for application to photodynamic therapy against superficial bladder tumor using precursor 5-aminolevulinic acid," Keio Igaku, 1994, 71(6):T221-T236, with partial English translation.
Kimura et al., "Photosensitizing agent and light equipment in photodynamic therapy in dermatology area," Visual Dermatology, Jul. 2008, 31:52-56, with partial English translation.
Matsumoto et al., "Preparing guidelines for treating skin tumor by photodynamic therapy (PDT)," Jpn. J. Dermatol., 2010, 120(13):2955-2957.
van der Veen et al., "Photobleaching during and re-appearance after photodynamic therapy of topical ala-induced fluorescence in UVB-treated mouse skin," Int. J. Cancer, 1997, 72:110-118.
Wang et al., Biological Organic Photo-Chemistry, 2008, Science Press, p. 96, with English translation of last paragraph.
Fritsch et al., "Green light is effective and less painful than red light in photodynamic therapy of facial solar keratoses," Photodermatology Photoimmunology & Photomedicine, 1997, 13:181-185.
Mackenzie et al., "Optimal conditions for successful ablation of high-grade dysplasia in Barrett's oesophagus using aminolaevulinic acid photodynamic therapy," Lasers Med. Sci., 2009, 24:729-734.
Matsumoto et al., "PDT for skin disease," 25th Annual Meeting of the Japanese Skin Cancer Society, Feb. 25, 2010, (2):Workshop 2, 4 pages, with English translation, 2 pages.

* cited by examiner x100 517nm LED (Mouse No. 1)   x400 517nm LED (Mouse No. 1)

x100 629nm LED (Mouse No. 2)   x400 629nm LED (Mouse No. 2)

x100 no irradiation (Mouse No. 3)   x400 no irradiation (Mouse No. 3)

PHOTODYNAMIC THERAPY USING PHOTOSENSITIZING AGENT OR 5-AMINOLEVULINIC ACID

CROSS-REFERENCE TO RELATED APPLICATIONS

This application is a National Stage application of PCT/JP2012/003995, filed Jun. 20, 2012, which claims priority from Japanese application JP 2011-147711, filed Jul. 1, 2011.

TECHNICAL FIELD

The present invention relates to photodynamic therapy using a photosensitizing agent or 5-aminolevulinic acids, and more specifically to photodynamic therapy involving administering a photosensitizing agent or 5-aminolevulinic acids followed by irradiation with excitation light at a wavelength of 480 to 580 nm.

BACKGROUND ART

Photodynamic therapy is a therapy utilizing the cell-killing capability of reactive oxygen species including singlet oxygen generated by administering a photosensitizing agent and accumulating it in an affected area, followed by light excitation. The photodynamic therapy has attracted attention in recent years because it is a noninvasive therapy less likely to leave a therapy scar. It is also known that most of compounds used as photosensitizing agents have a structure called tetrapyrrole, have absorption spectrum peaks representing characteristic strong absorbance around a wavelength of 400 nm and absorption spectrum peaks around wavelengths of 600 to 700 nm, and specifically accumulate in tumor tissue and new blood vessels. Cells of tumor tissue and new blood vessels are considered to be capable of being degenerated/necrotized by singlet oxygen produced by using light corresponding to the peak of the absorption spectrum of a photosensitizing agent as excitation light to irradiate the photosensitizing agent accumulating in tumor tissue and new blood vessels; the therapy of a disease of the skin surface such as acne by irradiation with light at a short wavelength around 400 nm and the therapy of cancer by irradiation with light at a long wavelength around 600 to 700 nm having a relatively good capability of deep tissue penetration and the like are performed (see for example, Patent Document 1).

Although 5-aminolevulinic acid (hereinafter also referred to as "ALA") is one natural amino acid contained in a living body, broadly present in animals, plants, and fungi, ALA has no photosensitivity per se; however, protoporphyrin IX (hereinafter also referred to as "PpIX") produced by its metabolic activation by a series of enzymes of the heme biosynthetic pathway in cells is known as a photosensitizing agent showing peaks at 410 nm, 545 nm, 580 nm, 630 nm, and the like (Non-patent Document 1), and work is proceeding on 5-aminolevulinic acid-based photodynamic therapy (hereinafter also referred to as "ALA-PDT") which involves accumulating PpIX in cancer cells followed by irradiation with excitation light around 600 to 700 nm to degenerate/necrotize cells of an affected part (see for example, Patent Documents 2 to 9).

PRIOR ART DOCUMENTS

Patent Documents

Patent Document 1
Japanese unexamined Patent Application Publication No. 2011-001307
Patent Document 2
Japanese unexamined Patent Application Publication No. 2010-163445
Patent Document 3
Japanese unexamined Patent Application Publication No. 2008-208072
Patent Document 4
Japanese unexamined Patent Application Publication No. 2007-015938
Patent Document 5
Japanese unexamined Patent Application Publication No. 2006-182753
Patent Document 6
Japanese unexamined Patent Application Publication No. 2005-350418
Patent Document 7
Japanese unexamined Patent Application Publication No. 2005-349028
Patent Document 8
Japanese unexamined Patent Application Publication No. 2005-132766
Patent Document 9
Japanese unexamined Patent Application Publication No. 11-012197

Non-patent Documents

Non-patent Document 1
Yoshiya Matsumoto, Maruho Hifuka Seminar (Dermatology Seminar) "Kohsenrikigaku Ryohoh (Photodynamic Therapy, PDT)" aired on Feb. 25, 2010, from The 25th Annual Meeting of the Japanese Skin Cancer Society (2): Workshop 2

SUMMARY OF THE INVENTION

Object to be Solved by the Invention

Factors inhibiting the capability of deep tissue penetration of excitation light in photodynamic therapy (PDT) and photodynamic diagnosis (PDD) are considered to be mainly fat, hemoglobin, melanin, and the like. Generally, light at a wavelength around 400 nm has a low capability of deep tissue penetration although it is suitable for the excitation of a photosensitizing agent because of its high energy. In addition, as also shown, for example, from FIG. 1 on the absorption spectrum of hemoglobin inhibiting the deep penetration of light in a living body (R. R. Anderson et al., J. invest dermatol 77, 13-19 (1981)), the light at a wavelength around 400 nm is strongly subject to the light-absorbing action of hemoglobin, which further decreases its capability of deep tissue penetration. Thus, the light at a wavelength around 400 nm is efficient in the diagnosis and therapy of a surface layer part but cannot pass through the blood or fat tissue; thus, it has been difficult to use it for the diagnosis or therapy of parts requiring a certain degree of the capability of deep penetration, such as subcutaneous cancer and lymph nodes surrounded by blood and fat.

As also shown from FIG. 1, the light-absorbing action of hemoglobin is known to be weak in the range on the side of a wavelength longer than 600 nm; however, light of a wavelength longer than 600 nm has a relatively high capability of deep penetration but is low in energy and inefficient in terms of the excitation of a photosensitizing agent. Thus, in PDT, even the use of light having large optical power density requires a long light irradiation time, which has been a burden for a patient.

An object of the present invention is to provide PDT and PDD which reduce the burden of a patient and are suitable for the diagnosis and therapy of a part requiring a certain degree of deep penetration, such as subcutaneous cancer and lymph nodes surrounded by blood vessels and fat.

Means to Solve the Object

The present inventors have focused attention on the fact that the absorbance of pigments of biological origin such as hemoglobin and bilirubin is reduced around 480 to 580 nm as shown in the FIG. 1, and the cell-killing effect of each wavelength on cancer cells was examined either without light shielding by hemoglobin, imitating the surface of a living body, or with light shielding by hemoglobin, imitating the inside of a living body. Without the light shielding by hemoglobin, no difference in the optical power density between wavelengths was observed, whereas with the light shielding by hemoglobin, the optical power density became 0 with light at 402 nm and also significantly reduced with light at wavelengths of 502 to 529 nm compared to that with light at 636 nm (see FIG. 3). The cell-killing effect was higher with light at 502 to 529 nm than with light at 636 nm, and with light at 402 nm than with light at 502 to 529 nm without the light shielding by hemoglobin, but surprisingly, even with the light shielding by hemoglobin, the cell-killing effect at wavelengths of 502 to 529 nm was higher or almost the same as that with light at 636 nm; thus, it was found that even a low optical power density would result in a high therapeutic effect with light at wavelengths of 502 to 529 nm.

Thus, the present invention relates to: (1) a composition comprising a photosensitizing agent or a5-aminolevulinic acids for photodynamic therapy comprising irradiation with excitation light at a wavelength of 480 to 580 nm; (2) the composition according to (1) above, wherein the photodynamic therapy comprises irradiating cancer with excitation light at a wavelength of 480 to 580 nm; and (3) the composition according to (1) or (2) above, wherein the excitation light has a wavelength of 500 to 530 nm.

The present invention also relates to (4) a method for photodynamic therapy, comprising administering a photosensitizing agent or 5-aminolevulinic acids followed by irradiation with excitation light at a wavelength of 480 to 580 nm.

Effect of the Invention

The use of the light around 500 nm of the present invention can more efficiently excite a photosensitizing agent than the use of light at a wavelength longer than 600 nm, and enables the improvement of the effect of PDT and PDD and the shortening of the therapy/diagnosis time thereof and also enables PDT and PDD in a deep part into which light of 400 nm cannot penetrate.

MODE OF CARRYING OUT THE INVENTION

Figure 1:
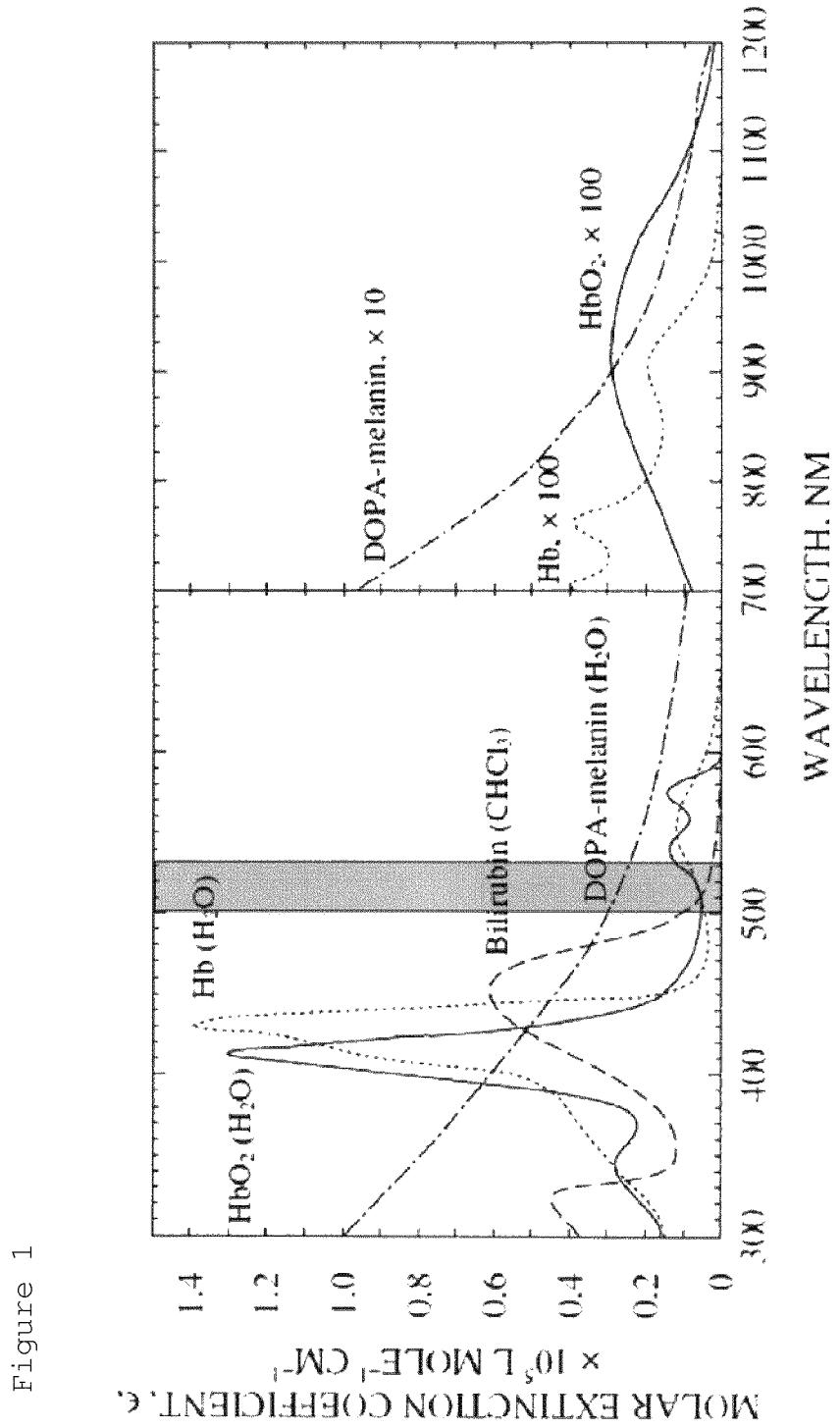
FIG. 1 is a graph regarding the absorption spectrum of hemoglobin, which inhibits the deep penetration of light in a living body.

The present invention relates to a composition comprising a photosensitizing agent or 5-aminolevulinic acids for PDT and PDD involving irradiation with excitation light at a wavelength of 480 to 580 nm, preferably a wavelength of 500 to 530 nm, and a method for photodynamic therapy which involves administering a photosensitizing agent or 5-aminolevulinic acids followed by irradiation with excitation light at a wavelength of 480 to 580 nm, preferably a wavelength of 490 to 570 nm, more preferably a wavelength of 500 to 550 nm, still more preferably 500 to 530 nm; as the subject of PDT there can be preferably exemplified superficial and subcutaneous cancers such as warts, cervical cancer, skin cancer, thyroid cancer, and malignant brain tumor, especially several millimeter-deep subcutaneous cancer and as the subject of PDD there can be preferably exemplified sentinel lymph nodes. Pre-removal lymph node metastasis diagnosis can be carried out by PDD.

The photosensitizing agent capable of absorbing visible light to emit fluorescence and generate active oxygen may be any agent provided that it is a photosensitizing agent used for PDT and PDD; however, a tetrapyrrole-based compound can be preferably exemplified, among others. Specific examples thereof include photofrin, Laserphyrin, protoporphyrin IX, Foscan, chlorin, uroporphyrin I, uroporphyrin III, heptacarboxylporphyrin I, heptacarboxylporphyrin III, hexacarboxylporphyrin I, hexacarboxylporphyrin III, pentacarboxylporphyrin I, pentacarboxylporphyrin III, coproporphyrin I, coproporphyrin III, isocoproporphyrin, harderoporphyrin, isoharderoporphyrin, hematoporphyrin, mesoporphyrin, etioporphyrin, pyrroporphyrin, deuteroporphyrin IX, pemptoporphyrin, and ATXs-10. The dose thereof is the same as that recommended for PDT with visible light.

For the purpose of the present invention, 5-aminolevulinic acids (ALAs) refers to 5-aminolevulinic acid (ALA) or a derivative thereof, or a salt of the 5 aminolevulinic acid or the derivative. ALA is a well-known compound, weakly absorbs visible light per se, and generates no fluorescence or active oxygen under light irradiation; however, it advantageously acts as a photosensitizing agent because of being metabolized to protoporphyrin as a photosensitizing substance in the body after administration. The accumulation of protoporphyrin IX when ALAs are administered is specific for lesions such as cancer, dysplasia, bacteria/fungi-infected parts, and virus-infected cells, and the ALAs act as the most promising photosensitizing agent because they are also highly safe compounds.

ALA or a derivative thereof is represented by formula (I) below (where $R^1$ represents a hydrogen atom or an acyl group, and $R^2$ represents a hydrogen atom, a straight-chain or branched alkyl group, a cycloalkyl group, an aryl group, or an aralkyl group).

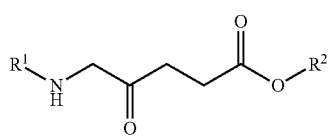

(I)

Among ALAs, there can be preferably exemplified ALA, in which $R^1$ and $R^2$ in the formula (I) each represent a hydrogen atom, or a salt thereof. ALA is one amino acid called δ-aminolevulinic acid. Examples of the ALA derivative include a compound other than 5-ALA, in which $R^1$ in the formula (I) represents a hydrogen atom or an acyl group and $R^2$ in the formula (I) represents a hydrogen atom, a straight-chain or branched alkyl group, a cycloalkyl group, an aryl group, or an aralkyl group.

Examples of the acyl group in the formula (I) include straight-chain or branched alkanoyl groups each having 1 to 8 carbons, such as a formyl group, an acetyl group, a propionyl group, a butyryl group, an isobutyryl group, a valeryl group, an isovaleryl group, a pivaloyl group, a hexanoyl group, an octanoyl group, and a benzylcarbonyl group, and aroyl groups each having 7 to 14 carbons, such as a benzoyl group, a 1-naphthoyl group, and a 2-naphthoyl group.

Examples of the alkyl group in the formula (I) include straight-chain or branched alkyl groups each having 1 to 8 carbons, such as a methyl group, an ethyl group, a propyl group, an isopropyl group, a butyl group, an isobutyl group, a sec-butyl group, a tert-butyl group, a pentyl group, an isopentyl group, a neopentyl group, a hexyl group, a heptyl group, and an octyl group.

Examples of the cycloalkyl group in the formula (I) include cycloalkyl groups each having 3 to 8 carbons and optionally containing saturated or partially unsaturated bond, such as a cyclopropyl group, a cyclobutyl group, a cyclopentyl group, a cyclohexyl group, a cycloheptyl group, a cyclooctyl group, a cyclododecyl group, and a 1-cyclohexenyl group.

Examples of the aryl group in the formula (I) include aryl groups each having 6 to 14 carbons, such as a phenyl group, a naphthyl group, an anthryl group, and a phenanthryl group.

The aralkyl group in the formula (I) has an aryl moiety to which the same exemplification as that of the above-described aryl group can be applied and an alkyl moiety to which the same exemplification as that of the above-described alkyl group can be applied; specific examples thereof include aralkyl groups each having 7 to 15 carbons, such as a benzyl group, a phenethyl group, a phenylpropyl group, a phenylbutyl group, a benzhydryl group, a trityl group, a naphthylmethyl group, and a naphthylethyl group.

The ALA derivative is preferably a compound in which $R^1$ represents a formyl group, an acetyl group, a propionyl group, a butyryl group, or the like, or a compound in which $R^2$ represents a methyl group, an ethyl group, a propyl group, a butyl group, a pentyl group, or the like; preferred examples of the combination of $R^1$ and $R^2$ include combinations of: a formyl group and a methyl group; an acetyl group and a methyl group; a propionyl group and a methyl group; a butyryl group and a methyl group; a formyl group and an ethyl group, an acetyl group and an ethyl group; a propionyl group and an ethyl group; and a butyryl group and an ethyl group.

ALAs each need only to act as an active ingredient in the form of ALA or a derivative thereof of the formula (I) in a living body, and may be administered as any of various salts or esters for the enhancement of solubility or a prodrug (precursor) capable of being decomposed by an enzyme in a living body, depending on the dosage form. Examples of the salt of ALA and a salt of the derivative include pharmacologically acceptable acid addition salts, metal salts, ammonium salts, and organic amine addition salts. Examples of the acid addition salt include inorganic acid salts such as hydrochlorides, hydrobromates, hydroiodides, phosphates, nitrates, and sulfates, and organic acid addition salts such as formates, acetates, propionates, toluenesulfonates, succinates, oxalates, lactates, tartrates, glycolates, methanesulfonates, butyrates, valerates, citrates, fumarates, maleates, and malates. Examples of the metal salt include alkali metal salts such as lithium salts, sodium salts, and potassium salts; alkali earth metal salts such as magnesium salts and calcium salts; and metal salts such as aluminum salts and zinc salts. Examples of the ammonium salt include ammonium salts and alkylammonium salts such as tetramethylammonium salts. Examples of the organic amine salt include salts such as triethylamine salts, piperidine salts, morpholine salts, and toluidine salts. These salts can also be used as solutions at the time of use.

Among the above ALAs, preferred are ALA, various esters such as ALA methyl ester, ALA ethyl ester, ALA propyl ester, ALA butyl ester, and ALA pentyl ester, and hydrochlorides, phosphates, and sulfates thereof; ALA hydrochloride and ALA phosphate can be particularly preferably exemplified.

The above ALAs may form hydrates or solvates, and may be used alone or in a proper combination of two or more thereof. Those ALAs may also be used that are produced by any of methods of chemical synthesis, microbe-based production, and enzyme-based production.

When the above ALAs are each prepared as an aqueous solution, to prevent the decomposition of each ALA, care should be exercised so that the aqueous solution does not become alkaline. When it becomes alkaline, the decomposition can be prevented by removing oxygen.

In the composition of the present invention, if necessary, carriers such as a stabilizer, a dispersant, a solvent, a bulking agent, a nutrient, and an excipient are added to a photosensitizing agent or ALAs. As the blended carriers, carrier materials are used which are organic or inorganic solids or liquids suitable for ingestion and are typically inactive and pharmaceutically acceptable; specific examples of the carrier include crystalline cellulose, gelatin, lactose, starch, magnesium stearate, talc, vegetable and animal fat and oil, gum, and polyalkylene glycol. Examples of the dosage form of the composition of the present invention when used as a therapeutic agent include injections, drops, intravesical infusions, tablets, capsules, subtle granules, syrups, poultices, and suppositories.

Most of the above tetrapyrrole-based photosensitizing agents are administered by intravenous injection or drip infusion. Without being limited to intravenous injection and drip infusion, various forms of administration, such as oral administration (including sublingual administration), transdermal administration (by poultices or the like), suppository, and intravesical infusion are applicable to the ALAs; however, oral administration is advantageous considering the burden of a patient. The dose of ALAs is 1 mg to 100 mg, preferably 10 mg to 50 mg, more preferably 15 mg to 25 mg, still more preferably 20 mg, per kg body weight in terms of ALA hydrochloride.

In the case of typical PDD using ALAs or a photosensitizing agent, violet-colored visible light having a high excitation efficiency is irradiated and absorbed by the Soret band of the photosensitizing substance, and the affected area is diagnosed by emitted red fluorescence. Because it is a technology generally used for the diagnosis of a shallow part, the determination of an excision part during surgery, and the like, violet-colored light having a low degree of deep penetration appears to have no problem; however, the violet-colored visible light cannot excite a photosensitizing substance in actual surgery or the like because fat tissue is often present in the surface layer of the affected area and the violet-colored light is absorbed by the fat. The reality is that, for example, when cancer metastasis in the sentinel lymph node or the like is subjected to PDD, it is necessary to perform excision, followed by cutting to observe the cut surface.

In the case of PDD using the photodynamic diagnostic agent of the present invention, the irradiated excitation light can pass through the skin and thin fat tissue because it is light at a wavelength of 480 to 580 nm, enabling sufficient observation even from above the skin and fat. Such observation without excision is good news for QOL.

The light source for irradiation with excitation light at a wavelength of 480 to 580 nm used may be a well-known one; examples thereof include LED, preferably a flash/light-type LED, and laser lights such as a semiconductor laser; however, LED for which a device is compact and advantageous in terms of cost and portability, especially a flash/light-type LED, can be preferably exemplified. Highly sensitive and quantitative PDD can also be performed by guiding laser light of 480 to 580 nm using an optical fiber to highly intensely excite an intended part and simultaneously guiding PpIX-emitted fluorescence to a spectroscope to detect a fluorescence spectrum typical of PpIX.

The present invention will be specifically described below with reference to Examples. However, these Examples are not intended to limit the technical scope of the present invention.

EXAMPLES

Example 1

Study of Cell-Killing Effect of ALA-PDT Due to Difference in Wavelength

MKN45 cells (purchased from Riken Cell Bank) cultured in a 35-mm dish were cultured for 4 hours in the presence of 0.168 mg/mL ALA. Then, 5 mL of a hemoglobin solution was dispensed into a 60-mm dish, placed on the 35-mm dish in which the culture was performed in the presence of ALA, and irradiated with light. Light shielding by hemoglobin was provided to imitate the inside of a living body because hemoglobin is considered to be a leading cause of the inhibition of light invasion in photodynamic therapy. The culture was irradiated to 4.5 J/cm$^2$ (5 mW/cm$^2$, 15 min.) with light having a peak at 402 nm, 502 nm, 517 nm, 529 nm, or 636 nm. As control, without light shielding by hemoglobin, the culture was irradiated by using the same method except for the use of a phosphate buffer solution in place of the hemoglobin solution.

Figure 2:
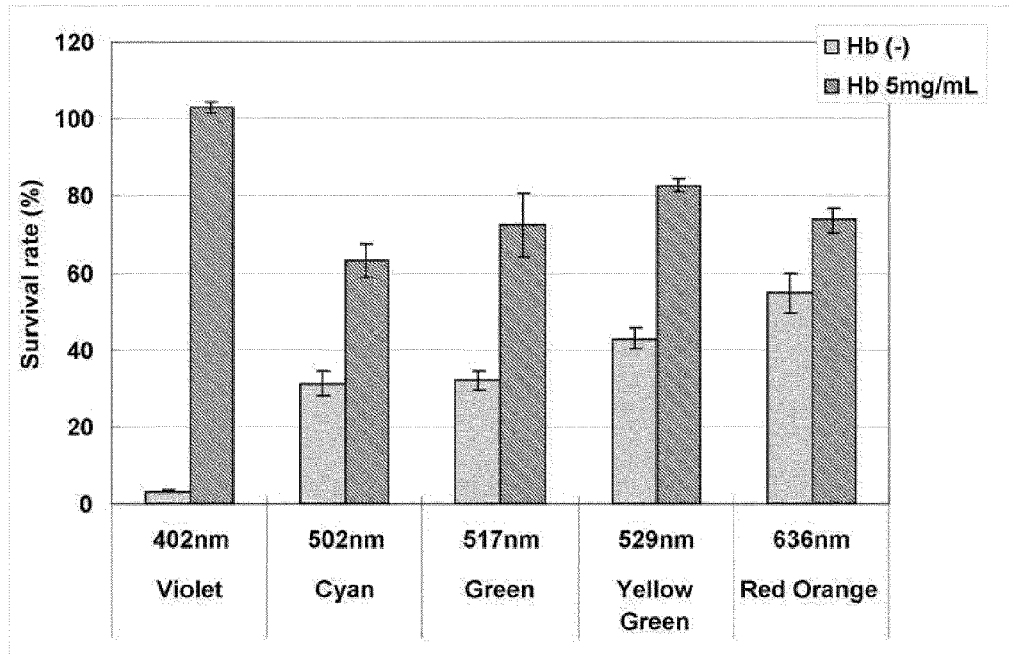
FIG. 2 is a graph showing the results of the cell-killing effect of ALA-PDT depending on differences in the wavelength in the presence and absence of light shielding by hemoglobin.
Figure 3:
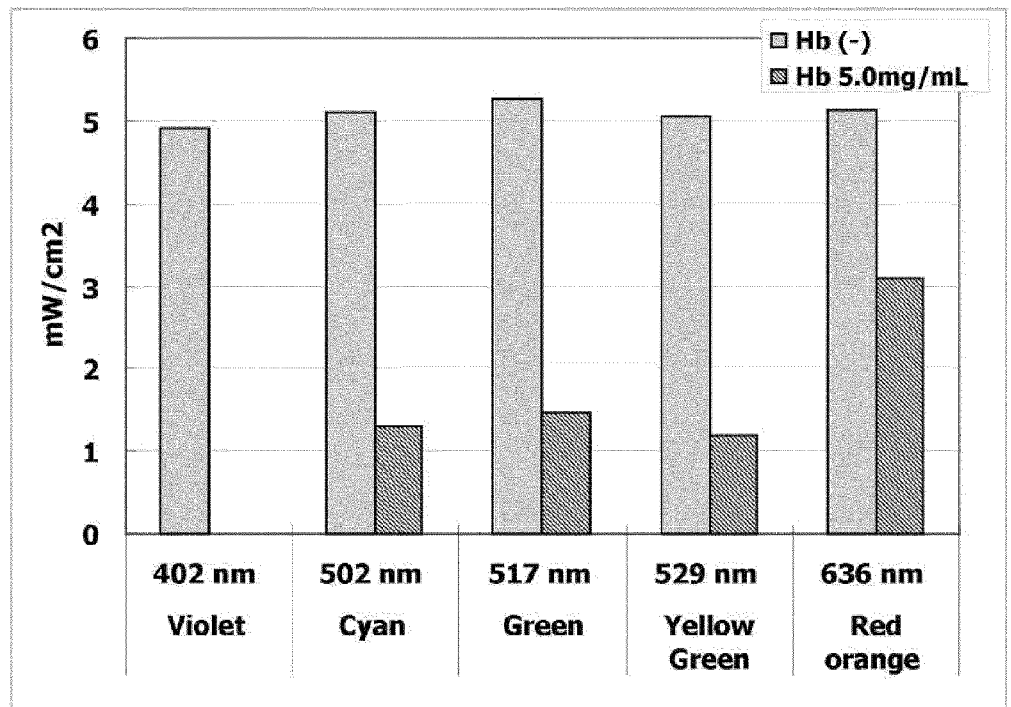
FIG. 3 is a graph showing the results of measurement of optical power density depending on differences in the wavelength in the presence and absence of light shielding by hemoglobin.

The survival rate of cells after light irradiation was measured using an MTT assay method. The MTT reagent (3-[4,5-dimethylthiazol-2-yl]-2,5-diphenyltetrazolium bromide) was dissolved in methanol to 50 mg/mL, which was used after 1:10 dilution with the phosphate buffer solution at the time of use. At a lapse of 24 hours from the irradiation of each of the above excitation lights, 200 µL of the MTT reagent was added per one 35-mm dish (2 mL) in which MKN45 cells were cultured, which was then allowed to stand for 4 hours in a $CO_2$ incubator. After standing, 2 mL of a 10% SDS solution was added, which was again allowed to stand overnight in the $CO_2$ incubator. Thereafter, 200 µL thereof was dispensed into a 96-well plate and measured for absorbance at 570 nm using a plate reader (from Bio-Rad). The survival rate was measured from the absorbance of each sample and expressed relative to the absorbance after a medium without cultured cells were subjected to these procedures, set to 0%, and the absorbance after such cells cultured as control were subjected to these procedures, set to 100%. The results are shown in FIG. 2. Optical power density with light shielding by hemoglobin was measured using Power Meter (from Scientex, Inc.); the results are shown in FIG. 3.

(Result)

As shown in FIG. 2, the cell-killing effect of ALA-PDT, without light shielding by hemoglobin, was stronger in the order of lights having a peak at 402 nm, 502 nm, 517 nm, 529 nm, or 636 nm (left bars). This agrees with the order of wavelengths having higher PpIX excitation efficiency. Thus, it is expected that the case without light shielding by hemoglobin would have the same effect also in the skin surface because this case is intended for the case where ALA-PDT is performed on the skin surface.

As also shown in FIG. 2, the cell-killing effect of ALA-PDT, with light shielding by hemoglobin, was observed with lights having a peak at 502 nm, 517 nm, 529 nm, or 636 nm (right bars); however, the cell-killing effect of ALA-PDT was not observed with light having a peak at 402 nm. These results confirmed that the wavelength around 400 nm resulted in the increased excitation efficiency of PpIX but in the decreased capability of deep tissue penetration, and was unsuitable for subcutaneous therapy because it could not cause the excitation in a deep part.

As shown in FIG. 3, lights having a peak at 402 nm, 502 nm, 517 nm, 529 nm, or 636 nm had similar optical power densities without light shielding by hemoglobin (left bars); however, the optical power densities of penetrated lights at 502 nm, 517 nm, and 529 nm were low compared to the optical power density of light at 636 nm with light shielding by hemoglobin (right bars).

The above confirmed that with light shielding by hemoglobin, lights at 502 nm, 517 nm, and 529 nm had low optical power densities but provided comparable cell-killing effects compared to light at 636 nm. Thus, it can be said that wavelengths around 480 to 580 nm retain the deep tissue penetration capability of light and have high PpIX excitation efficiencies compared to that of 636 nm.

Example 2

Study of Cancer Therapeutic Effect of ALA-PDT Depending on Difference in Wavelength $5 \times 10^5$ HeLa cells were subcutaneously injected into SCID mice of the mouse numbers 1 to 3. The size of tumors in the 3 SCID mice into which $5 \times 10^5$ HeLa cells were subcutaneously injected is shown in Table 1 below. Tumors about 4 mm in height were confirmed to be present in the mouse subcutis. After maintaining the mice until the size of tumors reaches that described in Table 1, 750 mg/kg b.w. of ALA was injected into the tail vein of the mice of numbers 1 and 2. After 4 hours, the mouse of number 1 was irradiated with LED light having a peak at a wavelength of 517 nm and the mouse of number 2 was irradiated with LED light having a peak at a wavelength of 629 nm.

TABLE 1

| Mouse No. | ALA | Tumor Size (mm) | | | Irradiation Light (100 J/cm² each) | |
|---|---|---|---|---|---|---|
| | | Major Diameter | Minor Diameter | Height | 517 nm (Green) | 629 nm (Red) |
| 1 | (+) | 13.0 | 10.0 | 3.7 | (+) | (−) |
| 2 | (+) | 10.3 | 9.0 | 4.1 | (−) | (+) |
| 3 | (−) | 12.0 | 9.1 | 4.6 | (−) | (−) |

Figure 4:
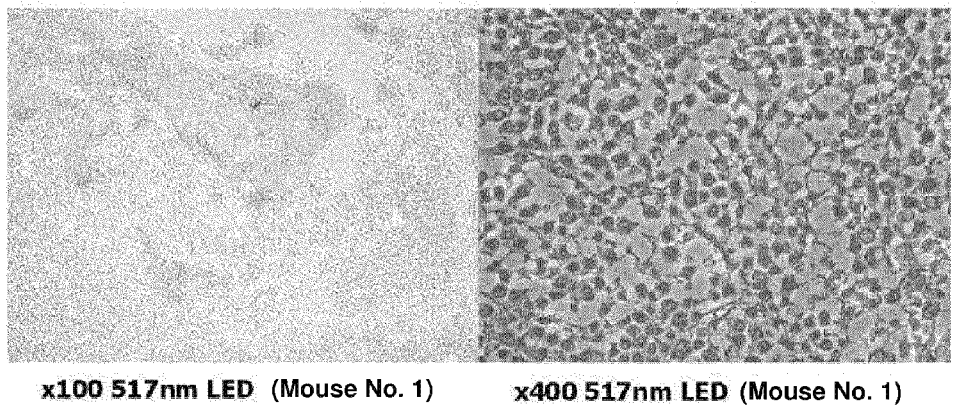
FIG. 4 is a series of photographs showing the results of hematoxylin-eosin staining regarding the cancer cell-killing effect of ALA-PDT depending on differences in the wavelength in mice.
Figure 4:
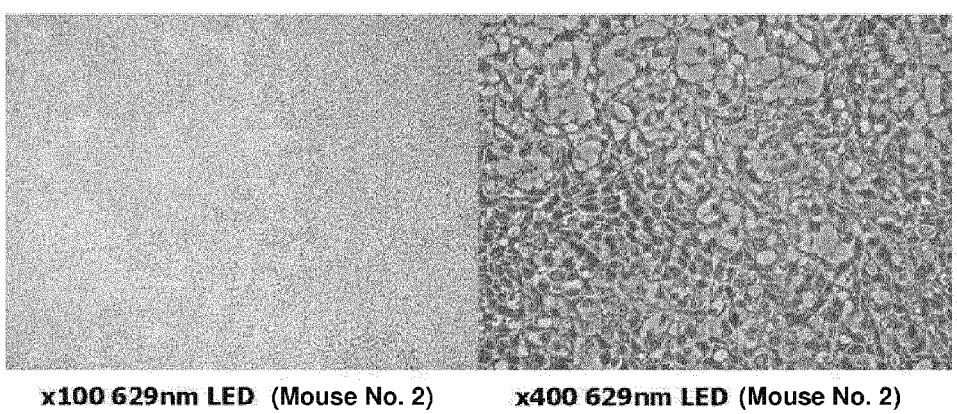
Figure 4:
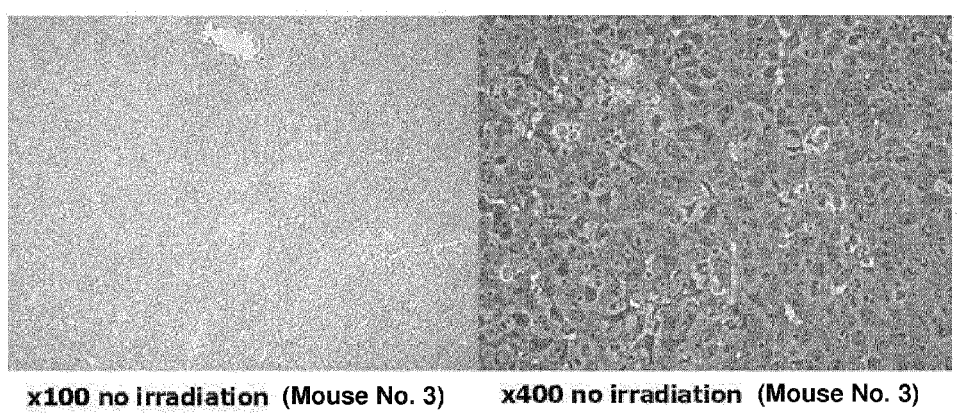

The SCID mice irradiated with light listed above were each anesthetized on the following day; a portion containing HeLa cells was cut out, fixed in formaldehyde, subjected to dehydration treatment with ethanol and xylene, and then embedded in paraffin; and a small piece thinly sliced into a thickness of 5 μm was stained with hematoxylin-eosin to observe the tissue under a light microscope. The results are shown in FIG. 4.

(Result)

Although cancer cells can be confirmed to be surviving in the microscope photograph of the mouse of number 3 not irradiated with light, the condensation of the cytoplasm, the disappearance of the nucleus, and clearance between cells due to the generation of blebs were observed in cells of the mice of numbers 1 and 2, indicating the effect of ALA-PDT. When cells of mice of numbers 1 and 2 were compared, for cells of the mouse of number 1 irradiated with light at 517 nm, the amount of blebs generated was estimated to be larger because the density of the cells was lower, confirming that the effect of ALA-PDT was higher. Thus, for a disease in a position at least up to 4 mm in depth, it was shown that light with a peak at a wavelength of 517 nm can deeply penetrate the affected area and ALA-PDT using light at this wavelength is more effective than that using light having a peak at a wavelength of 629 nm.

INDUSTRIAL APPLICABILITY

The PDT and PDD of the present invention are useful in the fields of medical therapy/diagnosis.

The invention claimed is:

1. A method for photodynamic therapy of a subcutaneous cancer or a method for photodynamic diagnosis of a sentinel lymph node, in a patient in need of said therapy or diagnosis, comprising orally administering to the patient a composition comprising 5-aminolevulinic acid or a salt thereof followed by irradiating the subcutaneous cancer or sentinel lymph node with an excitation light at a wavelength of 500 to 530 nm.

2. The method for photodynamic therapy or the method for photodynamic diagnosis according to claim 1, comprising orally administering to the patient a composition comprising 5-aminolevulinic acid or a salt thereof followed by irradiating the subcutaneous cancer with an excitation light at a wavelength of 500 to 530 nm.

3. The method for photodynamic therapy or the method for photodynamic diagnosis according to claim 1, comprising orally administering to the patient a composition comprising 5-aminolevulinic acid or a salt thereof followed by irradiating the sentinel lymph node with an excitation light at a wavelength of 500 to 530 nm.

* * * * *